United States Patent [19]

Wennerholm

[11] Patent Number: 5,301,689
[45] Date of Patent: Apr. 12, 1994

[54] DEVICE FOR TEMPORARY ARTIFICIAL RESPIRATION ASSISTANCE FOR PERSONS HAVING SNORE PROBLEMS

[75] Inventor: Bjorn Wennerholm, Göteborg, Sweden

[73] Assignee: Breas Medical AB, Gothenburg, Sweden

[21] Appl. No.: 28,769

[22] PCT Filed: Jun. 27, 1990

[86] PCT No.: PCT/SE90/00464

§ 371 Date: Dec. 27, 1991

§ 102(e) Date: Dec. 27, 1991

[87] PCT Pub. No.: WO91/00075

PCT Pub. Date: Jan. 10, 1991

Related U.S. Application Data

[63] Continuation of Ser. No. 781,144, Dec. 27, 1991, abandoned.

[30] Foreign Application Priority Data

Jun. 27, 1989 [SE] Sweden ............... 8902313-9

[51] Int. Cl.$^5$ .................. A61F 5/56; A62B 18/02
[52] U.S. Cl. .................. 128/848; 128/205.25
[58] Field of Search ........... 128/846, 848, 863, 205.13, 128/207.12, 206.11, 207.18, 204.18, 204.21, 205.25

[56] References Cited

U.S. PATENT DOCUMENTS

| | | | |
|---|---|---|---|
| 862,867 | 6/1907 | Eggleston . | |
| 3,058,463 | 10/1962 | Goodrich | 128/863 |
| 3,315,672 | 4/1967 | Cunningham | 128/863 |
| 3,625,207 | 12/1971 | Agnew | 128/863 |
| 3,747,599 | 7/1973 | Malmin | 128/863 |
| 4,004,299 | 1/1977 | Runge . | |
| 4,323,064 | 4/1982 | Hoenig | 128/204.21 |
| 4,489,723 | 12/1984 | Simons | 128/859 |
| 4,493,614 | 1/1985 | Chu et al. . | |
| 4,593,686 | 6/1986 | Lloyd | 128/848 |
| 4,686,974 | 8/1987 | Sato et al. . | |
| 4,686,975 | 8/1987 | Naimon | 128/207.18 |
| 4,944,310 | 7/1990 | Sullivan | 128/848 |

FOREIGN PATENT DOCUMENTS

| | | |
|---|---|---|
| 2647378 | 10/1975 | Fed. Rep. of Germany . |
| 2520422 | 11/1975 | Fed. Rep. of Germany ...... 128/859 |
| 88/10108 | 12/1988 | PCT Int'l Appl. . |
| 1541852 | 3/1979 | United Kingdom . |

Primary Examiner—Michael A. Brown
Attorney, Agent, or Firm—Merchant & Gould, Smith, Edell, Welter & Schmidt

[57] ABSTRACT

Device for temporary breathing assistance at snoring problems during sleep and curing of obstructive sleep apnea by means of a source (34) of pressurized air connected to the air passages of the sleeping person via a breathing mask (32). A sensor (30) is arranged inside or at the breathing mask (32), which sensor is designed to connect said pressurized air source (34), by way of a control apparatus (36) during a controllable period of time, e.g. corresponding to some breaths, which pressurized air source is provided to emit a certain amount of air with a settable respiratory positive pressure, which can cure the sleeping apnea.

5 Claims, 2 Drawing Sheets

DEVICE FOR TEMPORARY ARTIFICIAL RESPIRATION ASSISTANCE FOR PERSONS HAVING SNORE PROBLEMS

This is a file wrapper continuation of application Ser. No. 07/781,144, filed Dec. 27, 1991, now abandoned.

The present invention refers to a device for temporary breathing assistance at snore problems during sleep and curing of obstructive sleep apnea by means of a source of pressurized air connected to the air passages of the sleeping person via a breathing mask.

BACKGROUND OF THE INVENTION

Since the beginning of the eighties, when the illness obstructive sleep apnea syndrome was defined, which implies breathing interrupts or breaks in the normal breathing activity during sleep, which is mostly caused by obstruction of the upper air passages, several different methods have been tested, to find out a suitable treatment. Except for operations a so called CPAP (Continous Positive Airway Pressure) method has come into use to an ever increasing extent. Despite some drawbacks, the CPAP- method has shown good treatment results, by the reduction of the day sleepiness which is for example very hazardous when driving a car, and the sleep will be calmer and the characteristic loud snoring will disappear. The CPAP apparatus, which consists of a continously operating radial fan, which is driven by a 100 W electric motor, and a reduction valve, is set on an individual pressure level for respective patient, gives via a tube and a nose mask a continous positive pressure of about 10 mbar, in the breathing passages, which is often satisfactory. Drawbacks as expiration resistance, impossible to use at cold, risk of infection in sinus and ear ducts, drying out of mucous membranes in the nose and mouth at blowing through of excess air (about 4 liters/sec) which the fan delivers, often occurs when the mouth is opened during the sleep, as a rule is tolerated by the patient, but is very troublesome. Despite the relatively high price of the apparatus, this is lower than the cost for the operation, at the same time as considerably less medical treatment is demanded. The level of cost is however of great importance since the calculated need in Sweden is about 100.000 apparatuses, and the cost about 1,2 milliard SEK with present level of price. In addition to this a two days sleeping test at a hospital is required, before the patient can obtain an apparatus for domestic use (OSAS is regarded as a cronical disease). The problem also has another dimension, namely that some traffic accidents, where single road-users as well as drivers of public services are involved has to be charged on the account of sleep apnea, which thus constitute a great latent danger. Very few OSAS- patients are aware of their illness before they have been tested. Fatigue and a bad general condition is often believed to depend on other factors.

In the European patent no 88761 the snoring problem has been attacked by means of nose mask, which is connected to an air pump of high volume type, which during the complete sleeping period continously provides a static air pressure, which is slightly higher than the athmospherical pressure. The drawback of this device is the above mentioned problems. In order to reduce the drying of the mucous membranes, one has even suggested to tape together the mouth during the night, so that the breathing only occurs through the nose, but this drastic measure is for obvious reasons extremely uncomfortable, but illustrates that the side-effects cannot be ignored.

The CPAP- system, which means a continous static air pressure, does not work at the often occuring centrally conditioned apnea contributions in OSAS ( Obstructive Sleep Apnea Syndrome). The static pressure holds the breathing paths open but can not accomplish pulsing breathing activity, which stops at central apneas.

CPAP implies, in addition to said drawbacks that air is pressed into the stomach/intestinal tract at swallowing reflexes, which are provoked by the continous positive pressure, which leads to discomfort. It has also been discovered an increase of the pressure in the cerebrospinal fluid which can have not yet defined consequencies, e.g. balance disorder. A risk of otitis also is present, which might cause a hearing loss.

The device according to said EP 88761 has been developed further, in WO 88/10108, according to which the nose mask is connected to a microphone, the output signal of which via a prcessor unit controls the speed of the motor which drives a fan wheel. In relation to arising to snoring sounds the speed of the motor is increased, and thereby the pressure and the output amount of air. Through this apparatus, during periods when no snoring is present, the continously output amount of air kan be kept on a lower level, whereby the expiration resistance can be kept smaller and thereby also less troublesome. However the tendency of drying up of the mucous membranes is still very troublesome, as well as the increased risk for infection in the sinus and the circumstance that the apparatus cannot be used at common colds. Another drawback is that the impulse generating snoring sounds are individual and irregular, and occur mainly at the end of an apnea period in connection to the sleeping patient himself being able to cure the breathing obstruction. Sound impulses moreover can occur through sleep talking, teeth grinding, caughing and so forth, and externally, why the method is not reliable to cure apnea at the right moment, that is before lack of oxygen occurs in the blood. There is also a risk that that the pressure is elevated at the wrong point of time, so that the sleeping patient is woken up. This system does not supervise loss of breathing, but reacts first on the after-effects (snoring) thereof. Moreover the drawback remains of high energy consumption (portable petrol engines or battery powered devices), even if this has been minimized by the temporarily reduced fan speed.

THE OBJECT OF THE INVENTION AND MOST IMPORTANT FEATURES

The object of the invention is to provid a device which:
a) supervises every breath;
b) controls the breathing activity from falling asleep to waking up;
c) gives a substantially less drying up of the mucous membranes;
d) is useful even at nasal congestion, e.g. common colds;
e) effectively cures breath stop;
f) makes possible a counter pressure free expiration;
g) substantially reduces medical after-effects;
h) does not require an individual pressure setting;
i) is not activated by sound impulses;
j) simple, reliable design;

k) low energy consumption;
l) low manufacturing cost;

These problems have been solved by a sensor arranged inside or at the breathing mask, which sensor is designed to connect said pressurized air source, by way of a control apparatus during a controllable period of time, e.g. corresponding to some breaths, which pressurized air source is provided to emit a certain amount of air with a settable respiratory positive pressure, which can cure the sleeping apnea.

DESCRIPTION OF THE DRAWINGS

The invention will be described in more detail in some embodiments with reference to the drawings.

DESCRIPTION OF EMBODIMENTS

Figure 1:
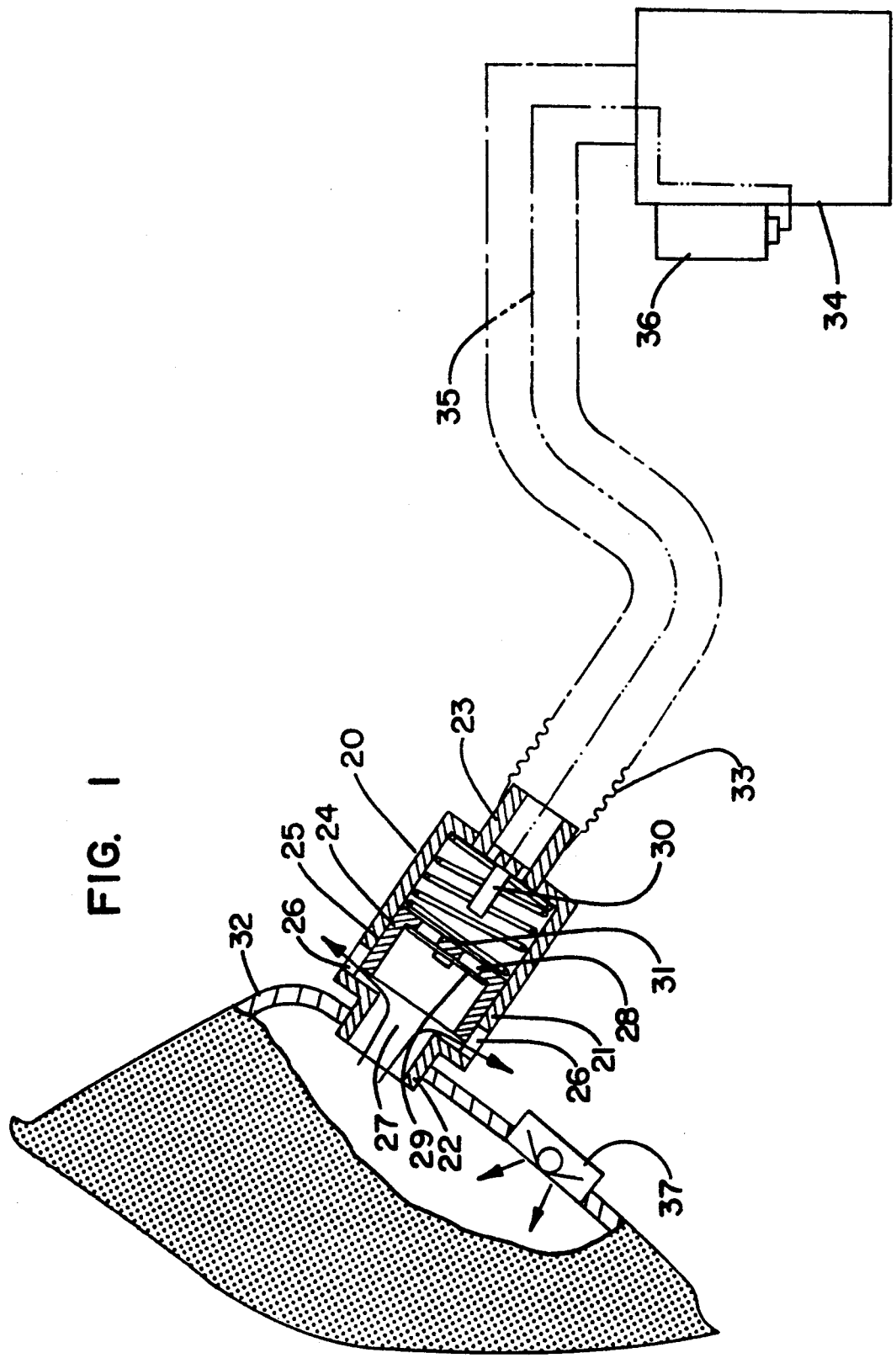
FIG. 1 shows diagrammatically the device according to the invention partly in section.

The device according to the invention consists of a breathing apparatus 20, which contains a cylinder 21 with a connection pipe 22,23 in both ends. Inside the cylinder 21 is provided a displaceable piston 24, which is a part of an expiration valve 25, and which is kept by a spring 38 in one of its end positions, in which it closes at least one opening 26 bored in the cylinder. The piston is provided such that the expiration air versus the action of the spring 25 is pressed into mthe cylinder 21, so that the openings 26 are set free and the breathing air can leave the breathing apparatus 20. The piston 24 in the piston bottom provided with a nonreturn valve 27 in the form of openings 28, which are covered by a valve washer 29, e.g. a metal foil. At one of the connection pipes 23 an inductive sensor 30 is mounted, which sensor cooperates with a metal head 31 at one of the bottom surfaces of the piston 24.

The breathing apparatus 20 with one of its connection pipes 22 is connected to a breathing mask 32, which is formed to cover as well the nose as the mouth. The other connection pipe 23 is by way of a pipe 33 connected to a source of pressurized air 34, which can be a piston or bellows pump, but also an air accumulator which can be supplied by a fan or the like. The source of air pressure 34 has to be dimensioned such that it by demand directly can emit a volume of air corresponding to at least 1-2 breaths. The sensor 30 by means of a cable 35 connected to an electrical control apparatus 36 and at the rate of the reciprocating motion emits pulses to the control apparatus 36, which is designed such, that it activates the source of pressurized air 34, if after a settable time period one or several pulses should be missing as a result of breath stop. The amount of air emitted by the source of pressurized air flows in the form of a light pressure impact against the piston 24 and passes through the nonreturn valve 27 and into the airways.

The inhalation takes place by way of nonreturn valves 37 provided in the breathing mask 32, which open at every breath intake, but closes at the expiration.

When the breathing, which normally occurs with intervals of five seconds, stops, the sleeping patient recieves an air pulse of about 1, 5 liters with an initial pressure which exceeds the apnea threshold of the person and there by opens the airways. The volume of the supplied air pulse is calculated to compensate at least 2 missing breaths of 0, 5 liters each. If the natural breathing activity is not started after the cure of the apnea, the procedure is repeated after 10–15 second until a natural breathing is initiated. By using a system of the described type, a continous postive pressure is avoided in the airways with described negative consequences. There is no need for calibrating the auxillary assembly to specific pressure levels, since the pressure goes down as soon as the airways are opened. The volume of the auxillary air pulse of 1,5 liters is less than a half of the total lung volume of an adult, but gives compensation for 2–3 lost breaths at rest (during sleep). According to requirements the assembly may assist the breathing during the total sleeping period thereby prevent that a lack of oxygen results to any appreciable extent. The energy consumption is less than 40 W or about 3 Ah at 12 Volts during a sleeping period of 7 hours, which makes it possible to operate with rechargeable or standard batteries during at least one sleeping period at maximum operation. A so called heavy apnea patient has up to 500 breathing stops per night and som tens of apneas are not unusual. In such cases the battery capacity lasts for one week or more, before a recharge or exchange is necessary.

Supervision of the breathing activity is carried out by means of the inductive sensor 30 placed at the breathing apparatus 20 in the face mask 32. When the valve piston 24 with the nonreturn valve 27 is moving at the inspiration or expiration, the sensor 30 emits an electric pulse to the control apparatus 36. This supervises pulse trains emitted from the sensor, and which can be set between e.g. 1-10 sec. The output remains at rest as long as the time between the pulses is shorter than the time set. If the time between the pulses exceeds the time set, an output relay will be activated during about 3 sec. Thereafter the relay returns and the supervision is resumed. The relay can have several closing and breaking functions. This supervisory system reacts rapidly and reliable even on one missing breath and breathing assistance is then engaged before lack of oxygen in blood occurs.

Figure 2:
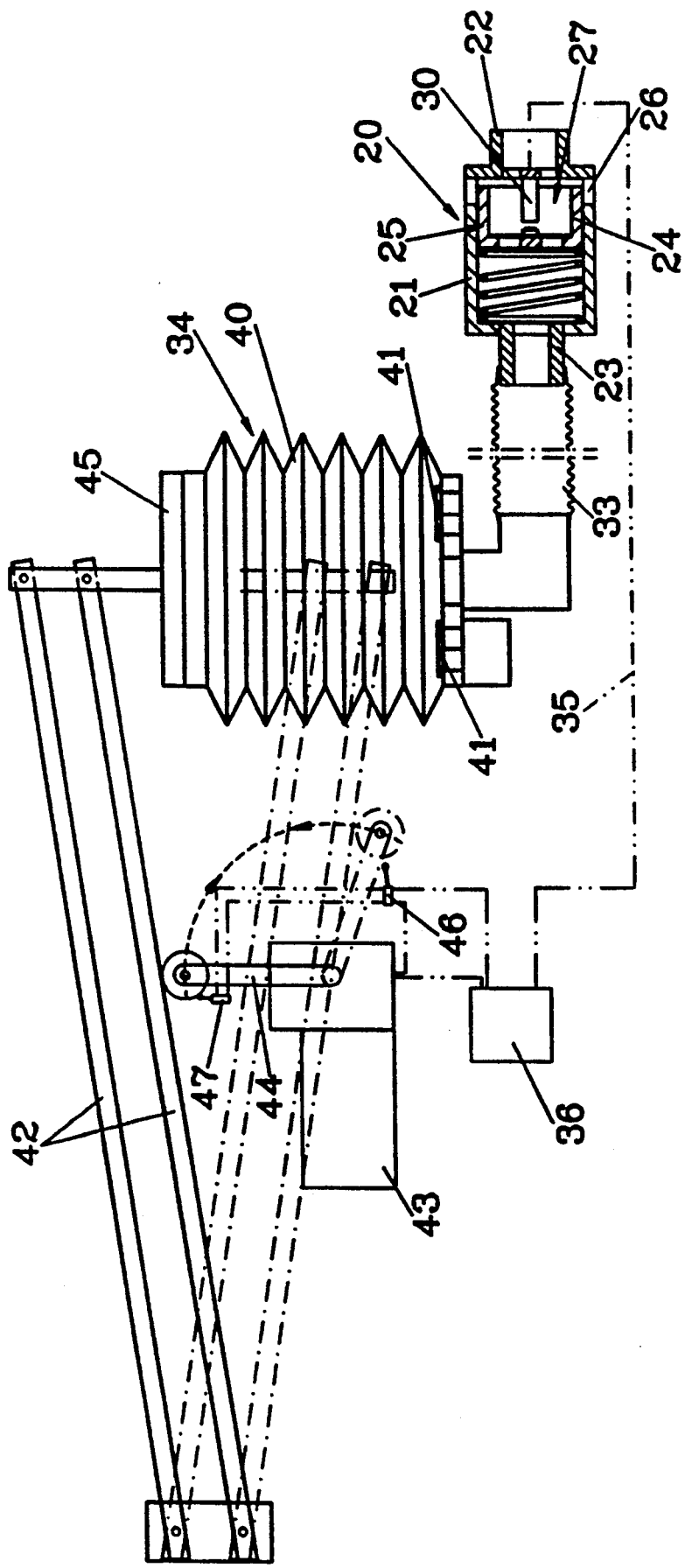
FIG. 2 shows a modified embodiment of the device according to FIG. 1 equally partly in section.

The air pulse which is required to open the airways at sleep apnea according to the invention can be generated by a folded belows 40—FIG. 2—, which through a valve system 41 can be filled and emptied on a certain air volume by mechanical actuation. The mainly linear movement is provided by a parallell arm 42, which is lifted by an electric pendulum motor 43, and is lowered by a weight 44 or by means of spring force, which gives the suitable specific pressure and the flow velocity for apnea curing and breathing assistance. The lifting effect can also be provided by electric or pneumatic control apparatus, arranged such that only the lifting movement is forced, while the sinking movement takes place freely, only actuated by gravitational or spring force, which has been preset. This arrangement prevents that a pressure higher than the preset can be established in the airways, at the same time as the flow velocity is adapted to the breathing rhythm of the patient.

In order to make it possible to cure an apnea which has occurred by a certain air pulse volume, the expiring function of the breathing apparatus has to be blocked during the time period the blowing in takes place. This can be carried out by an electromagnet which is placed close to the valve membrane, whereby the electromagnet locks the valve membrane to the seat of the valve, during the blowing period, about 2 sec, by the magnet recieving current from the control apparatus during corresponding time. The expiration valve 25 alternatively can be blocked by the positive pressure of the discharge air, as is shown in FIG. 1. Irrespective of which method will be used, a blocking of the expiration valve 20 during the discharge is to prefer to a contracted outlet without a valve, since this degrades the intended effect, at the same time as an expiration resistance is formed at normal breathing activity.

The stated system and the apparatus for breathing assistance at sleeping apnea can be used alternatively for blowing in through nose or mouth since the relatively small air quantities which are used do not have any appreciable drying up effect on the mucous membranes. This increases the utility of the system substantially, e.g. general colds, which has ben mentioned earlier. By using a so called halv mask of the type similar to that used in the industry and which covers both nose and mouth, the risk for so called feedback is eliminated. This is of particular importance in connection to the intermittent system which is comprised by the invention if this shall have an optimal function, since here is used an adapted amount of air for every curing of apnea. The advantage to be able to breathe through the nose alternatively the mouth, as has been mentioned above, of course is applicable in this case.

When going to bed the patient fixes the breathing mask 32 against the face by means of attachment bands, and switches on the starting switch of the assembly. The breathing goes on unimpededly through the valve system of the mask during the falling asleep, with a breath of 0,5 liters per second an pulses are simultaneously from the sensor 30 to the control apparatus 34. If this is set on e.g. 10 seconds and if no pulse arrives because the breathing has stopped, the relay is actuated which closes a current circuit to the electric motor 43 of the pressure source. Its pendulum arm 44 then performs a movement directed downwards and releases a weight loaded parallel arm 42, which comprimates the bellows 34 with a pressure defined by gravitational force of the weight 45. Since the pendulum arm 42, actuated by a switch 46, has parked at its lower turning point, the enclosed air volume of the bellows, about 1,5 liters, can be delivered by way of the tube 33 to the breathing mask 32 of the patient the pressure of the mask being balanced for curing of the apnea and a preset flow velocity under a regressive fall of pressure. When the bellows has been emptied and the parallel arm has reached the bottom standby position, the current circuit to the pendulum motor is closed through a shifting function in a rely (not shown), whereby the pendulum arm 44 and the parallel arm 42 returns to the upper stand by position, where the current circuit is broken by a switch 47. In connection hereby the weight 45 is lifted the bellows 40 expands and is filled with air via a nonreturn valve 41 and a suction filter 48. This procedure is repeated within about 10 seconds if the apnea is not cured after the previous air pulse, and thus no electric pulses from the sensor are emitted to the control unit. In adition to the pulse frequency the pressure, volume and blowing time can be adjusted to the most suitable values for effective curing of apnea and not to disturb the sleep of the patient unnecessarily.

I claim:

1. An apparatus for temporary assistance for relieving a sleeping person from obstructed sleep apnea, comprising:
   a breathing mask adapted to cover the nose or mouth of said sleeping person;
   an electric motor-driven source of pressurized air connected to said mask with a flexible tube;
   isolation means for maintaining the space enclosed by said mask and said tube isolated from the atmosphere in the absence of inspiration or expiration of said sleeping person;
   an expiratory valve operatively connected to said isolation means, said expiratory valve being actuated by the expiratory air of said sleeping person;
   detection means for detecting a pause in the breathing rhythm of said sleeping person and for activating in response thereto said source of pressurized air to deliver a predefined amount of air into said space to create a gradually increasing positive air pressure in said mask until said pressure is sufficient for relieving said sleeping apnea, said detection means comprising a sensor, operatively connected to said isolation means, to emit pulses to a control apparatus connected to said source of pressurized air in response to movement of said expiratory valve; and
   means for stopping said source of pressurized air when a resumed breathing of said sleeping person is detected by said detection means.

2. The apparatus according to claim 1, wherein said expiratory valve comprises a spring loaded piston displaceable within a cylinder, said cylinder provided with blow-off openings, wherein said openings in the on actuated position of said piston are blocked by said piston and which are open by the pressure actuation of the expiration air, said piston including a non-return valve provided to block the passage of the expiration air, but allows air to flow in the opposite direction; and wherein said sensor is arranged to detect movement of said piston.

3. The apparatus according to claim 1, wherein said breathing mask includes an inhalation valve.

4. The apparatus according to claim 1, wherein said pressurized air source comprises a piston or bellows horse pump, wherein the operating strokes of said piston or bellows are initiated by a controllable spring force or a variable weight and the return strokes of said piston or bellows are provided by a setting apparatus.

5. The apparatus according to claim 1, wherein said pressurized air source is arranged to emit an air pulse, the air volume of said air pulse corresponding to the air volume of at least two breaths of said sleeping person.

* * * * *